United States Patent

Hellendahl et al.

[11] Patent Number: 5,958,923
[45] Date of Patent: *Sep. 28, 1999

[54] USE OF THIAZOLE AND THIADIAZOLE COMPOUNDS

[75] Inventors: Beate Hellendahl, Schifferstadt; Annegret Lansky, Darmstadt; Beatrice Rendenbach-Müller, Neustadt; Alfred Bach, Heidelberg; Liliane Unger, Ludwigshafen; Hans-Jürgen Teschendorf, Dudenhofen; Karsten Wicke, Altrip, all of Germany

[73] Assignee: BASF Aktiengesellschaft, Ludwigshafen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/765,915
[22] PCT Filed: Jul. 14, 1995
[86] PCT No.: PCT/EP95/02783
    § 371 Date: Jan. 14, 1997
    § 102(e) Date: Jan. 14, 1997
[87] PCT Pub. No.: WO96/02249
    PCT Pub. Date: Feb. 1, 1996

[30] Foreign Application Priority Data

Jul. 15, 1994 [DE] Germany .............................. 44 25 145

[51] Int. Cl.⁶ .................... C07D 285/12; C07D 285/125; C07D 285/135; A61K 31/495
[52] U.S. Cl. .......................... 514/252; 514/256; 514/318; 514/241; 514/326; 514/333; 544/245; 544/367; 546/193; 546/209; 546/277
[58] Field of Search ..................................... 514/252, 256, 514/318, 326, 333, 241; 544/245, 367; 546/193, 209, 277

[56] References Cited

U.S. PATENT DOCUMENTS

| | | | |
|---|---|---|---|
| 3,522,846 | 8/1970 | New et al. ............................... | 166/303 |
| 3,717,651 | 2/1973 | Pilgram et al. ...................... | 260/306.8 |
| 4,074,049 | 2/1978 | Begin et al. ............................... | 544/82 |
| 4,935,424 | 6/1990 | Caprathe et al. ........................ | 514/252 |
| 4,943,580 | 7/1990 | Janssens et al. ........................ | 514/303 |
| 5,071,864 | 12/1991 | Rendenbach-Mueller .............. | 514/370 |
| 5,086,053 | 2/1992 | Brodin et al. ......................... | 514/236.2 |
| 5,401,743 | 3/1995 | Rendenbach-Mueller et al. .... | 514/252 |
| 5,401,762 | 3/1995 | Rendenbach-Mueller .............. | 514/369 |
| 5,418,235 | 5/1995 | Rendenbach-Mueller .............. | 514/252 |
| 5,424,312 | 6/1995 | Rendenbach-Mueller et al. .... | 514/252 |

FOREIGN PATENT DOCUMENTS

| | | |
|---|---|---|
| 282133 | 9/1988 | European Pat. Off. . |
| 0345533 | 5/1989 | European Pat. Off. . |
| 345533 | 12/1989 | European Pat. Off. . |
| 356333 | 2/1990 | European Pat. Off. . |
| 0409048 | 7/1990 | European Pat. Off. . |
| 1053085 | 3/1965 | United Kingdom . |
| 1053085 | 12/1966 | United Kingdom . |
| 1149110 | 3/1968 | United Kingdom . |
| 1149110 | 4/1969 | United Kingdom . |
| 89/11476 | 11/1989 | WIPO . |
| 92/07831 | 5/1992 | WIPO . |
| 9207831 | 5/1992 | WIPO . |
| 9222541 | 12/1992 | WIPO . |

OTHER PUBLICATIONS

Lowe et al., J. Med Chem. 1991, 34, 1860–1866.
*Drugs of the Future*, vol. 19, No. 6, 1994, pp. 560–563.
*J. Med. Chem.*, vol. 36, 1993, pp. 3929–3936.
*J. Med. Chem.*, vol. 34, 1991, pp. 1860–1866.

Primary Examiner—Jose' G. Dees
Assistant Examiner—Sabiha N. Qazi
Attorney, Agent, or Firm—Keil & Weinkauf

[57] ABSTRACT

The present invention relates to the use of thiazole and thiadiazole compounds of the following formula:

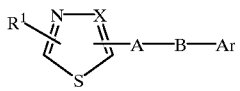

where $R^1$, A, B and Ar have the meanings stated in the description. The compounds according to the invention have a high affinity for the dopamine $D_3$ receptor and can therefore be used to treat disorders of the central nervous system.

11 Claims, No Drawings

USE OF THIAZOLE AND THIADIAZOLE COMPOUNDS

The invention relates to the use of thiazole and thiadiazole compounds. Said compounds have valuable therapeutic properties and can be used to treat disorders which respond to dopamine $D_3$ receptor ligands.

Compounds which are of the type under discussion here and have physiological activities have been disclosed. Thus, U.S. Pat. No. 4,074,049 describes aminoalkylthiothiadiazoles which act as fungicides and blood platelet aggregation inhibitors. JP-A-2 153 276 describes similar compounds which are used to treat liver disorders.

GB-A-1 053 085 describes aminoalkylthiadiazoles which show antitussive, analgesic, antipyretic and hypoglycemic effects. U.S. Pat. No. 3,717,651 describes 5-mercapto-substituted thiazoles which have herbicidal properties.

WO 89/11 476 describes substituted 2-aminothiazoles as dopaminergic agents which can be used, inter alia, for treating psychoses and disorders of the CNS.

WO 92/22 540 describes aminoalkyl-substituted 5-mercaptothiazoles of the formula:

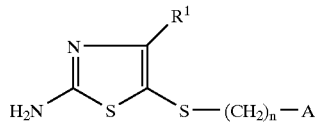

where $R^1$ is H, $C_1$–$C_5$-alkyl, unsubstituted or substituted phenyl or thienyl; n is 2–6; and A is

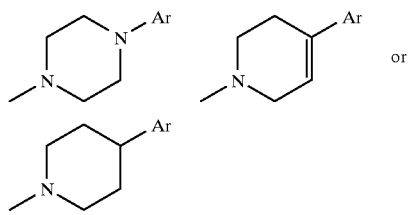

where Ar is a phenyl ring which is unsubstituted or substituted once by $C_1$–$C_5$-alkyl, $C_1$–$C_5$-alkoxy, amino, halogen, nitro, hydroxyl, trifluoromethyl or cyano, or a pyridyl, pyrimidinyl or thienyl radical. These compounds can be used to treat disorders of the central nervous system, eg. Parkinsonism, schizophrenia and disorders associated with elevated blood pressure.

WO 92/22 542 describes the corresponding 2-amino-5-mercapto-1,3,4-thiadiazole derivatives which can likewise be used to treat disorders of the central nervous system and disorders associated with elevated blood pressure.

WO 92/22 541 describes corresponding 2-amino-1,3,4-thiadiazole derivatives where the alkylene chain is linked directly, not via a sulfur atom, to the thiadiazole residue. These compounds can also be used for treating disorders of the central nervous system and disorders associated with elevated blood pressure.

WO 93/21 179 describes 1-aryl-4-(ω-amido-1-alkyl and ω-imido-1-alkyl)piperazine compounds. These compounds are dopamine $D_2$ receptor antagonists and $5$-$HT_{1A}$ receptor agonists. They can be used as antipsychotic agents, for example for treating schizophrenia.

Neurons receive their information inter alia via G protein-coupled receptors. There are numerous substances which exert their effect via these receptors. One of them is dopamine.

Confirmed findings on the presence of dopamine and its physiological function as neurotransmitter have been published. Cells which respond to dopamine are connected with the etiology of schizophrenia and Parkinson's disease. These and other disorders are treated with drugs which interact with dopamine receptors.

By 1990, two subtypes of dopamine receptors had been clearly defined pharmacologically, namely $D_1$ and $D_2$ receptors.

Sokoloff et al., Nature 1990, 347: 146–151, found a third subtype, namely $D_3$ receptors. They are expressed mainly in the limbic system. The $D_3$ receptors differ structurally from the $D_1$ and $D_2$ receptors in about half the amino-acid residues.

The effect of neuroleptics has generally been ascribed to their affinity for $D_2$ receptors. Recent receptor-binding studies have confirmed this. According to these, most dopamine antagonists, like neuroleptics, have high affinity for $D_2$ receptors but only low affinity for $D_3$ receptors.

The prior art compounds described above are such $D_2$ receptor agonists or antagonists.

We have now found, surprisingly, that the compounds according to the invention have a high affinity for the dopamine $D_3$ receptor and only a low affinity for the $D_2$ receptor. They are thus selective $D_3$ ligands.

The present invention therefore relates to the use of thiazole and thiadiazole compounds of the formula I:

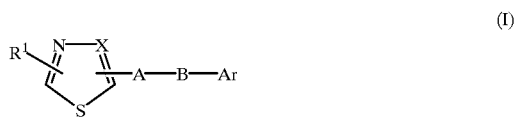

(I)

where

A is a straight-chain or branched $C_1$–$C_{18}$-alkylene group which may comprise at least one group selected from O, S, $NR^3$, $CONR^3$, $NR^3CO$, COO, OCO or a double or triple bond, B is a radical of the formula:

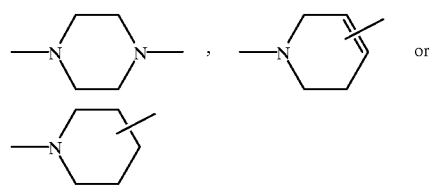

$R^1$ is H, halogen, CN, $CO_2R^2$, $NR^2R^3$, $OR^3$, $CF_3$ or $C_1$–$C_8$-alkyl, which is unsubstituted or substituted by OH, $OC_1$–$C_8$-alkyl or halogen;

$R^2$ is H, $C_1$–$C_8$-alkyl, which is unsubstituted or substituted by OH, $OC_1$–$C_8$-alkyl or halogen or phenyl-$C_1$–$C_8$-alkyl;

$R^3$ has the meanings indicated for $R^2$ or is $COR^2$ or $CO_2R^2$;

X is N or $CR^4$ where $R^4$ is H, $C_1$–$C_8$-alkyl which is unsubstituted or substituted by OH, $OC_1$–$C_8$-alkyl or halogen, or is phenyl which is unsubstituted or substituted by halogen, $CF_3$, $C_1$–$C_8$-alkyl or $C_1$–$C_8$-alkoxy;

Ar is phenyl, pyridyl, pyrimidyl or triazinyl, where Ar may have from one to four substituents which are selected, independently of one another, from H, $OR^3$, $C_1$–$C_8$-alkyl, $C_2$–$C_8$-alkenyl, $C_2$–$C_8$-alkynyl, halogen, CN, $CO_2R^2$, $NO_2$, $SO_2R^2$, $SO_3R^2$, $NR^2R^3$, $SO_2NR^2R^3$, $SR^2$, $CF_3$, $CH_2$, a 5- or 6-membered carbocyclic aromatic or non-aromatic ring and a 5- or 6-membered heterocyclic aromatic or non-aromatic ring having 1 to 3 hetero atoms selected from O, S and N, where the carbocyclic or the heterocyclic ring is unsubstituted or substituted by $C_1$–$C_8$-alkyl, halogen, $OC_1$–$C_8$-alkyl, OH, $NO_2$ or $CF_3$ and where Ar may also be fused to a carbocyclic or heterocyclic ring of the type defined above, and the salts thereof with physiologically tolerated acids for producing a pharmaceutical composition for treating disorders which respond to dopamine $D_3$ receptor antagonists or agonists.

The compounds used according to the invention are selective dopamine $D_3$ receptor ligands which intervene regioselectively in the limbic system and, because of their low affinity for the $D_2$ receptor, have fewer side effects than classical neuroleptics. The compounds can therefore be used to treat disorders which respond to dopamine $D_3$ receptor antagonists or agonists, eg. for treating disorders of the central nervous system, in particular schizophrenia, depression, neuroses and psychoses. They can additionally be used to treat sleep disorders and nausea and as antihistamines.

Within the scope of the present invention, the following terms have the meanings indicated below:

Alkyl (also in radicals such as alkoxy, alkylamino etc.) means a straight-chain or branched alkyl group having 1 to 8 carbon atoms, preferably 1 to 6 carbon atoms and, in particular, 1 to 4 carbon atoms. The alkyl group can have one or more substituents which are selected, independently of one another, from among OH and $OC_1$–$C_8$-alkyl.

Examples of an alkyl group are methyl, ethyl, n-propyl, i-propyl, n-butyl, isobutyl, t-butyl etc.

Alkylene stands for straight-chain or branched radicals having, preferably, 2 to 14 carbon atoms, particularly preferably 3 to 12 carbon atoms and, in particular, 7 to 12 carbon atoms.

The alkylene groups may comprise at least one of the abovementioned groups. This can—just like the double or triple bond mentioned—be arranged in the alkylene chain at any point or at the end of the chain so that it connects the chain to the thiazole or thiadiazole residue. The latter is preferred. When the alkylene group comprises a double or triple bond, it has at least three carbon atoms in the chain.

Halogen is F, Cl, Br, I and, in particular, F, Cl, Br.

$R^1$ is preferably H, $OR^3$ or $NR^2R^3$, where $R^2$ and $R^3$ are, independently of one another, H or $C_1$–$C_8$-alkyl.

Ar can have one, two, three or four substituents.

They are preferably selected, independently of one another, from H, $C_1$–$C_8$-alkyl which is unsubstituted or substituted by OH, $OC_1$–$C_8$-alkyl or halogen, or phenyl, naphthyl, $C_3$–$C_8$-cycloalkyl, a 5- or 6-membered heterocyclic aromatic or nonaromatic radical with 1 to 3 hetero atoms selected from O, N and S, $CHF_2$, $CF_3$, halogen, $NO_2$, CN, $OR^3$ or $SR^2$, where $R^2$ and $R^3$ have the abovementioned meanings.

If one of the substituents of Ar is $C_1$–$C_8$-alkyl, a branched radical, in particular the isopropyl or t-butyl group, is preferred.

Ar preferably has at least one substituent and is, in particular,

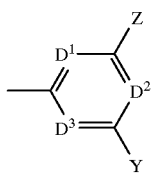

where $D^1$, $D^2$ and $D^3$ are, independently of one another, CR or N, and R, Y and Z are H or have the meanings indicated above or below.

Ar is preferably unsubstituted or substituted phenyl, 2-, 3- or 4-pyridinyl or 2-, 4(6)- or 5-pyrimidinyl.

When one of the substituents of Ar is a 5- or 6-membered heterocyclic ring, examples thereof are a pyrrolidine, piperidine, morpholine, piperazine, pyridine, pyrimidine, triazine, pyrrole, thiophene, thiazole, imidazole, oxazole, isoxazole, pyrazole or thiadiazole residue.

When one of the substituents of Ar is a carbocyclic radical, it is, in particular, a phenyl, cyclopentyl or cyclohexyl radical.

When Ar is fused to a carbocyclic or heterocyclic radical, Ar is, in particular, a naphthalene, di- or tetrahydronaphthalene, quinoline, di- or tetrahydroquinoline, indole, dihydroindole, benzimidazole, benzothiazole, benzothiadiazole, benzopyrrole or benzotriazole residue.

A preferred embodiment comprises the compounds of the formula I where A is $C_3$–$C_{14}$-alkylene, in particular $C_3$–$C_{12}$-alkylene, which may comprise at least one group selected from O, S, $NR^3$ and a double or triple bond.

Another preferred embodiment comprises the use of compounds of the formula I where $R^1$ is H, $OR^3$ or $NR^2R^3$, where $R^2$ and $R^3$ are, independently of one another, H, $C_1$–$C_8$-alkyl or phenyl-$C_1$–$C_8$-alkyl, $R^4$ is H or $C_1$–$C_8$-alkyl when X is $CR^4$;

A is $C_3$–$C_{12}$-alkylene which may comprise at least one group selected from O, S, $NR^3$ and a double or triple bond;

Ar is phenyl, pyrimidyl or pyridyl which may have one, two, three or four substituents which are selected, independently of one another, from H, $C_1$–$C_8$-alkyl which is unsubstituted or substituted by OH, $OC_1$–$C_8$-alkyl or halogen or phenyl, naphthyl, $C_3$–$C_8$-cycloalkyl, a 5- or 6-membered heterocyclic aromatic or nonaromatic radical with 1 to 3 hetero atoms selected from O, N and S, $CHF_2$, $CF_3$, halogen, $NO_2$, CN, $OR^3$ or $SR^2$, where $R^2$ and $R^3$ have the abovementioned meanings.

Particularly preferred compounds in this connection are those of the formula I where B is

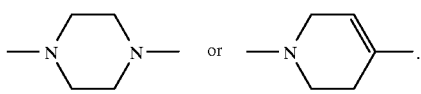

Another preferred embodiment is the use of the compounds of the formula I where

Ar is phenyl which has one, two, three or four substituents which are selected, independently of one another, from H, $C_1$–$C_8$-alkyl, phenyl, naphthyl, pyrrolyl, $CHF_2$, $CF_3$, halogen, $NO_2$, CN, OH, $OC_1$–$C_8$-alkyl, SH and $SC_1$–$C_8$-alkyl.

Ar is particularly preferably phenyl with one or two substituents in position 3 or position 3,5.

Another preferred embodiment is the use of compounds of the formula I where Ar is pyrimidinyl which has one to three substituents which are selected, independently of one another, from H, $C_1$–$C_8$-alkyl, $C_3$–$C_8$-cycloalkyl, phenyl, naphthyl, pyrrolyl, OH, $OC_1$–$C_8$-alkyl, $CHF_2$, $CF_3$ and halogen, or where Ar is pyridinyl which has one to four substituents which are selected, independently of one another, from H, $C_1$–$C_8$-alkyl, $C_2$–$C_8$-alkenyl, $C_2$–$C_8$-alkynyl, phenyl, naphthyl, pyrrolyl, OR, $OC_1$–$C_8$-alkyl, $CHF_2$, $CF_3$, CN and halogen.

The invention also relates to the compounds of the formula I where A is a straight-chain or branched $C_7$–$C_{18}$-alkylene group which may comprise a group which is selected from among O, S, $NR^3$, $CONR^3$, $NR^3CO$, COO, OCO or double or triple bond, and $R^1$, $R^3$, B and Ar have the abovementioned meanings.

The invention also embraces the acid addition salts of the compounds of the formula I with physiologically tolerated acids. Examples of suitable physiologically tolerated organic and inorganic acids are hydrochloric acid, hydrobromic acid, phosphoric acid, sulfuric acid, oxalic acid, maleic acid, fumaric acid, lactic acid, tartaric acid, adipic acid or benzoic acid. Other acids which can be used are described in Fortschritte der Arzneimittelforschung, Volume 10, pages 224 et seq., Birkhauser Verlag, Basel and Stuttgart, 1966.

The compounds of the formulae [sic] I may have one or more centers of asymmetry. The invention therefore includes not only the racemates but also the relevant enantiomers and diastereomers. The invention also includes the tautomeric forms in each case.

The compounds of the formulae [sic] I can be prepared by methods similar to conventional ones as described, for example, in Houben Weyl, "Handbuch der Organishen Chemie", Ernst Schaumann (Ed.), 4th Ed. Thieme Verlag, Stuttgart 1994, Volume Es/d, pages 189 et seq.; A. R. Katritzky, C. W. Rees (ed.) "Comprehensive Heterocyclic Chemistry", 1st Ed. and literature cited therein. The process for preparing the compounds comprises i) reacting a compound of the general formula II:

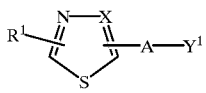

where $Y^1$ is a conventional leaving group, with a compound of the general formula III:

ii) to prepare a compound of the formula I where A comprises an oxygen or sulfur atom or $NR^3$,
a) reacting a compound of the general formula IV:

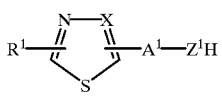

where $Z^1$ is O, S or $NR^3$, and $A^1$ is $C_0$–$C_{18}$-alkylene, with a compound of the general formula VI

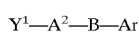

where $Y^1$ has the abovementioned meanings, and $A^2$ is $C_1$–$C_{18}$-alkylene, where $A^1$ and $A^2$ together have 7 to 18 carbon atoms;

iii) to prepare a compound of the formula I where A comprises the group COO or $CONR^3$:
a) reacting a compound of the general formula VII:

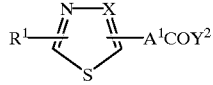

where $Y^2$ is OH, $OC_1$–$C_4$-alkyl, Cl or, together with CO, is an activated carboxyl group, and $A^1$ has the abovementioned meanings, with a compound of the formula VIII:

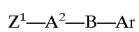

where $A^2$ has the abovementioned meanings, and $Z^1$ is OH or $NHR^3$, iv) to prepare a compound of the formula I where A comprises the group OCO or $NR^3CO$:
a) reacting a compound of the formula IV

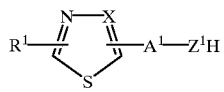

where $Z^1$ is O, or $NR^3$, with a compound of the formula X:

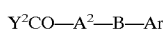

where $A^2$ and $Y^2$ have the abovementioned meanings, and where $R^1$, $R^2$, A, B and Ar have the abovementioned meanings.

To treat the abovementioned disorders, the compounds according to the invention are administered in a conventional manner orally or parenterally (subcutaneously, intravenously, intramuscularly, intraperitoneally). Administration can also take place with vapors or sprays through the nasopharyngeal space.

The dosage depends on the age, condition and weight of the patient and on the mode of administration. As a rule, the daily dose of active substance is about 10 to 1000 mg per patient and day on oral administration and about 1 to 500 mg per patient and day on parenteral administration.

The invention also relates to pharmaceutical compositions which contain the compounds according to the invention. These compositions are in the usual solid or liquid pharmaceutical administration forms, for example as tablets, film-coated tablets, capsules, powders, granules, sugar-coated tablets, suppositories, solutions or sprays. The active substances can in these cases be processed with conventional pharmaceutical aids such as tablet binders, fillers, preservatives, tablet disintegrants, flow regulators, plasticizers, wetting agents, dispersants, emulsifiers, solvents, release-slowing agents, antioxidants and/or propellant gases (cf. H. Sucker et al., Pharmazeutische Technologie, Thieme-Verlag, Stuttgart, 1978). The administration forms obtained in this way normally contain the active substance in an amount from 1 to 99% by weight.

The following examples serve to explain the invention without limiting it.

EXAMPLE 1

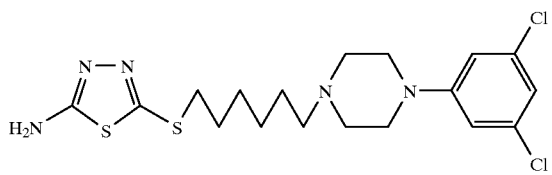

a) 2-Amino-5-(6-chlorohexylmercapto)-1,3,4-thiadiazole 5 g of 2-amino-5-mercapto-1,3,4-thiadiazole, 7.5 g of 1,6-bromochlorohexane [sic] and 4.07 g of triethylamine were refluxed in 100 ml of tetrahydrofuran for 1 hour. The mixture was filtered with suction, the filtrate was concentrated, and the residue was washed with water and then dried. 8.2 g (=91% yield) of product remained.

b) 2-Amino-5-(6-(3,5-dichlorophenylpiperazinyl) hexylmercapto)-1,3,4-thiadiazole) [sic]

2.2 g of product from 1a), 2.08 g of 3,5-dichlorophenylpiperazine and 1 g of triethylamine in 4 ml of DMF were heated at 100° C. for 1 hour. Water was added to the mixture and, after extracting 3 times with methylene chloride, drying over $MgSO_4$ and concentrating, the residue was purified by chromatography (mobile phase: $CH_2Cl/CH_3OH$ [sic]=9/1). 1.0 g (=25% yield) of product was obtained. Melting point: 130° C.

EXAMPLE 2 a) 5-Amino-2-(6-bromohexyl)-1,3,4-thiadiazole 5 g of 7-bromoheptanoic acid and 2.17 g of thiosemicarbazide were introduced into 50 ml of dioxane at 90° C. and, at this temperature, 4.0 g of $POCl_3$ were added dropwise. The mixture was then stirred at 90° C. for 1 hour. Then water was added to the mixture, and extraction 3 times with methylene chloride, drying over $MgSO_4$ and concentration were carried out. 6.1 g (=96% yield) of product were obtained as residue.

b) 2.5 g of product 2a), 2.18 g of u-trifluoromethylphenylpiperazine and 1.92 g of triethylamine in 3 ml of DMF were stirred at 100° C. for 1 hour. Workup took place as for 1b). 1.4 g (=36% yield) of product were obtained. Melting point: 134–136° C.

The compounds indicated in Tables 1 to 3 below were prepared in a similar manner.

The compounds listed in Tables 4 to 8 below can likewise be prepared in a similar manner.

TABLE 1

| No. | Example | physical data, H-NMR [&, ppm] mp. [° C.] |
|---|---|---|
| 3 | (structure: 5-amino-1,3,4-thiadiazole-S-propyl-piperazine-3-bromophenyl) | 1.8(2H); 2.4(6H); 3.08(2H); 3.13(4H); 6.9(2H); 7.05(1H); 7.12(1H); 7.3(2H) |
| 4 | (structure: 5-amino-1,3,4-thiadiazole-S-propyl-piperazine-phenyl-CN) | 1.8(2H; 2.43(6H); 3.1(2H); 3.18(4H); 7.1(1H); 7.25(4H); 7.35(1H) |
| 5 | (structure: 5-amino-1,3,4-thiadiazole-S-pentyl-piperazine-3-bromophenyl) | 191–194 |
| 6 | (structure: 5-amino-1,3,4-thiadiazole-S-pentyl-piperazine-3-chlorophenyl) | 140–143 |

TABLE 1-continued

| No. | Example | physical data, H-NMR [δ, ppm] mp. [° C.] |
|---|---|---|
| 7 | H₂N-[1,3,4-thiadiazole]-S-(CH₂)₆-N(piperazine)N-C₆H₄-Br (3-Br) | 117–119 |
| 8 | H₂N-[1,3,4-thiadiazole]-S-(CH₂)₅-N(piperazine)N-C₆H₄-CN (3-CN) | 1.5(4H); 1.8(2H); 2.4(2H); 2.6(4H); 3.18(2H; 3.22(4H); 5.1(2H); 7.1(3H); 7.3(1H) |
| 9 | H₂N-[1,3,4-thiadiazole]-S-(CH₂)₃-N(piperazine)N-C₆H₄-F (3-F) | 1.8(2H); 2.45(6H); 3.1(2H); 3.15(4H); 6.55(1H); 6.75(2H); 7.2(1H); 7.3(2H) |
| 10 | H₂N-[1,3,4-thiadiazole]-S-(CH₂)₅-N(piperazine)N-C₆H₄-Et (3-Et) | 1.25(3H); 1.5(4H); 1.78(2H); 2.4(2H); 2.6(6H); 3.2(6H); 5.1(2H); 6.75(3H); 7.2(1H) |
| 11 | H₂N-[1,3,4-thiadiazole]-S-(CH₂)₅-N(piperazine)N-C₆H₄-tBu (3-tBu) | 1.3(9H); 1.5(4H); 1.8(2H); 2.4(2H); 2.6(4H); 3.2(6H); 5.25(2H); 6.75(1H); 6.95(1H); 7.0(1H); 7.21(1H) |
| 12 | H₂N-[1,3,4-thiadiazole]-S-(CH₂)₅-N(piperazine)N-C₆H₄-OCH₂CH₃ (3-OEt) | 1.4(3H); 1.5(4H); 1.8(2H); 2.35(2H); 2.55(4H); 3.18(6H); 4.0(2H); 5.2(2H); 6.4(1H); 6.48(1H); 6.53(1H); 7.15(1H) |
| 13 | H₂N-[1,3,4-thiadiazole]-S-(CH₂)₃-N(piperazine)N-C₆H₃-Cl₂ (3,5-Cl₂) | 1.82(2H); 2.45(6H); 3.1(2H); 3.2(4H); 6.85(1H); 6.95(2H); 7.3(2H) |

TABLE 1-continued

| No. | Example | physical data, H-NMR [δ, ppm] mp. [° C.] |
|---|---|---|
| 14 | (structure: 2-amino-1,3,4-thiadiazole-S-(CH₂)₃-piperazine-3,5-dibromophenyl) | 146–149 |
| 15 | (structure: 2-amino-1,3,4-thiadiazole-S-(CH₂)₅-piperazine-3,5-dichlorophenyl) | 1.4(4H); 1.65(2H); 2.25(2H); 2.4(4H); 3.05(2H); 3.2(4H); 6.82(1H); 6.95(2H); 7.3(2H) |
| 16 | (structure: 2-amino-1,3,4-thiadiazole-S-CH₂-CH(CH₃)-CH₂-piperazine-3-CF₃-phenyl) | 96–110 |
| 17 | (structure: 2-amino-1,3,4-thiadiazole-S-(CH₂)₃-piperazine-3-SCH₃-phenyl) | 2.0(2H; 2.48(3H); 2.51(2H); 2.58(4H); 3.2(6H); 5.38(2H); 6.75(2H); 6.82(1H); 7.17(1H) |
| 18 | (structure: 2-amino-1,3,4-thiadiazole-S-(CH₂)₅-piperazine-3-SCH₃-phenyl) | 1.5(4H); 1.8(2H); 2.4(2H); 2.48(3H); 2.6(4H); 3.15(6H); 5.2(2H); 6.75(2H); 6.82(1H); 7.2(1H) |
| 19 | (structure: 2-methylamino-1,3,4-thiadiazole-S-(CH₂)₄-piperazine-3-CF₃-phenyl) | 1.7(2H); 1.8(2H); 2.4(2H); 2.6(4H); 3.05(3H); 3.15(2H); 3.22(4H); 5.7(1H); 7.1(3H); 7.35(1H) |
| 20 | (structure: 2-amino-1,3,4-thiadiazole-S-(CH₂)₅-piperazine-3-CHF₂-phenyl) | 1.55(4H); 1.8(2H); 2.4(2H); 2.6(4H); 3.2(2H); 3.25(4H); 5.15(2H); 6.6(1H); 7.0(2H); 7.03(1H); 7.32(1H) |
| 21 | (structure: thiazole-S-(CH₂)₃-piperazine-3-CF₃-phenyl) | 2.0(2H); 2.55(2H); 2.6(4H); 3.22(4H) 3.3(2H); 7.1(3H); 7.22(1H); 7.35(1H); 7.7(1H) |
| 22 | (structure: 2-amino-1,3,4-thiadiazole-S-(CH₂)₃-piperazine-3-isopropyl-phenyl) | 1.2(6H); 1.95(2H); 2.5(2H); 2.6(4H); 2.85(1H); 3.15(6H); 6.05(2H); 6.75(2H); 6.8(1H); 6.18(1H) |

TABLE 1-continued
| No. | Example | physical data, H-NMR [&, ppm] mp. [° C.] |
|---|---|---|
| 23 | 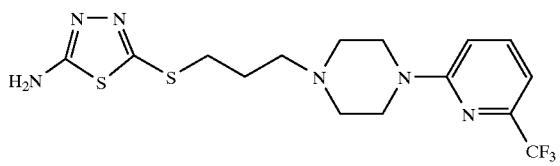 | 170–175 |
| 24 | 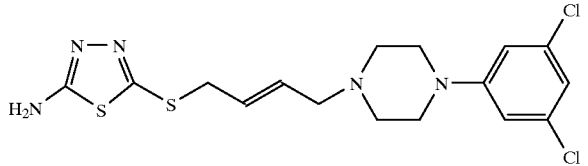 | 220–222 (Hydrochloride) |
| 25 | 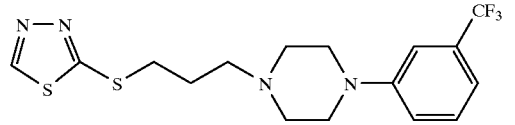 | 2.08(2H); 2.55(2H); 2.6(4H); 3.25(4H); 3.45(2H); 7.1(3H), 7.3(1H); 9.0(1H) |
| 26 | 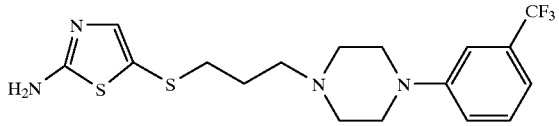 | 1.8(2H); 2.5(2H); 2.6(4H); 2.7(2H); 3.22(4H); 5.6(2H); 7.05(4H); 7.35(1H) |
| 27 | 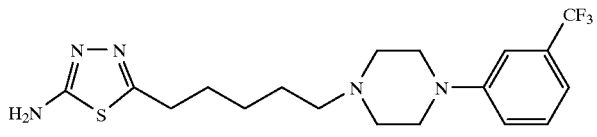 | 106–112 |
| 28 | 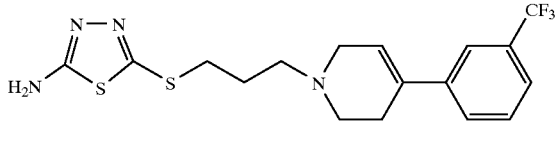 | 1.85(2H); 2.5(2H); 2.6(2H); 3.1(4H); 3.35(2H); 6.3(1H); 7.3(2H); 7.6(2H); 7.75(2H) |
| 29 | 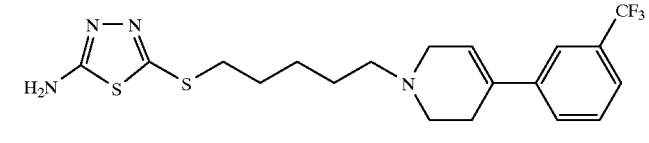 | 1.45(4H); 1.68(2H); 2.4(2H); 2.6(2H); 3.05(4H); 3.3(2H); 6.3(1H); 7.28(2H); 7.6(2H); 7.75(2H) |
| 30 | 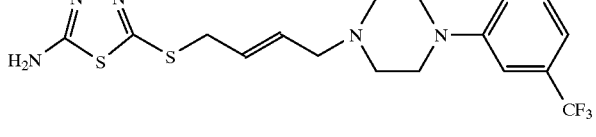 | 128–130 (Dihydrochloride) |
| 31 | 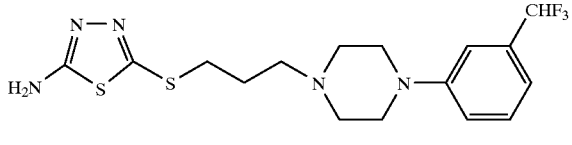 | 1.83(2H); 2.43(2H); 2.5(4H); 3.1(2H); 3.15(4H), 6.92(1H); 6.96(1H); 7.1(2H); 7.3(2H); 7.35(1H) |

TABLE 1-continued

| No. | Example | physical data, H-NMR [&, ppm] mp. [° C.] |
|---|---|---|
| 32 | [structure] | 129–130 |
| 33 | [structure] | 2.55(2H); 2.75(3H); 3.25(2H); 3.45(2H); 3.7(8H); 7.05(1H); 7.13(1H); 7.19(1H); 7.4(1H); (Dihydrochloride) |
| 34 | [structure] | 2.0(2H); 2.55(2H); 2.6(4H); 3.05(3H); 3.2(6H); 7.1(3H); 7.35(1H) |
| 35 | [structure] | 1.6(4H); 2.3(2H); 2.5(4H); 3.05(2H); 3.2(4H); 7.02(1H); 7.1(1H); 7.2(1H); 7.3(2H); 7.4(1H) |
| 36 | [structure] | 1.45(4H); 1.65(2H); 2.3(2H); 2.5(4H); 3.05(2H); 3.2(4H); 7.05(1H); 7.15(1H); 7.2(1H); 7.3(2H); 7.4(1H) |
| 37 | [structure] | 120 |
| 38 | [structure] | 188–190 (Trihydrachloride) |
| 39 | [structure] | 107–110 |
| 40 | [structure] | 131–132 |

TABLE 1-continued

| No. | Example | physical data, H-NMR [&, ppm] mp. [° C.] |
|---|---|---|
| 41 | 5-amino-1,3,4-thiadiazol-2-yl-S-(CH₂)₅-N(piperazine)N-(3-nitrophenyl) | 134–135 |
| 42 | 5-amino-1,3,4-thiadiazol-2-yl-(CH₂)₇-N(piperazine)N-(3-trifluoromethylphenyl) | 108–109 |
| 43 | 5-amino-1,3,4-thiadiazol-2-yl-(CH₂)₁₀-N(piperazine)N-(3-isopropylphenyl) | 140–141 |
| 44 | 5-amino-1,3,4-thiadiazol-2-yl-(CH₂)₁₀-N(piperazine)N-(3-cyanophenyl) | 137–139 |
| 45 | 5-amino-1,3,4-thiadiazol-2-yl-(CH₂)₁₀-N(piperazine)N-(3-difluoromethylphenyl) | 127–130 |
| 46 | 5-amino-1,3,4-thiadiazol-2-yl-(CH₂)₁₀-N(piperazine)N-(3-trifluoromethylphenyl) | 139–142 |

TABLE 2

Structure: $R^1$-(thiadiazole)-A-N(piperazine)N-(3-$R^6$-phenyl)

| Ex. No. | $R^1$ | $R^6$ | A | mp. [°C.] |
|---|---|---|---|---|
| 47 | NH₂ | CF₃ | S—CH₂C(CH₃)=CHCH₂— | 152–154° |
| 48 | NH₂ | CF₃ | S—(CH₂)₉— | 118–123° |
| 49 | NH₂ | iProp | S—(CH₂)₇— | 98–101° |
| 50 | NH₂ | CN | S—(CH₂)₇— | 162–166° |
| 51 | NH₂ | CN | S—(CH₂)₈— | 98–102° |
| 52 | NH₂ | iProp | S—(CH₂)₈— | 95–99° |

TABLE 3

Structure: $R^1$-(thiadiazole)-A-N(piperazine)N-(pyrimidine with $R^6$, $R^8$, D)

| Ex. No. | $R^1$ | $R^6$ | $R^8$ | D | A | mp. [°C.] |
|---|---|---|---|---|---|---|
| 53 | NH₂ | CF₃ | H | CH | S—CH₂CH=CHCH₂— | 116–119° |
| 54 | NH₂ | 1-Pyrrolyl | CH₃ | N | S—(CH₂)₅— | 145–148° |
| 55 | NH₂ | tBut | CF₃ | N | S—(CH₂)₃— | 128–130° |
| 56 | NH₂ | 1-Pyrrolyl | CH₃ | N | S—(CH₂)₃— | 130–132° |
| 57 | NH₂ | iProp | CF₃ | N | S—(CH₂)₃— | 109–111° |
| 58 | NH₂ | tBut | tBut | N | S—(CH₂)₃— | 142–145° |

TABLE 4

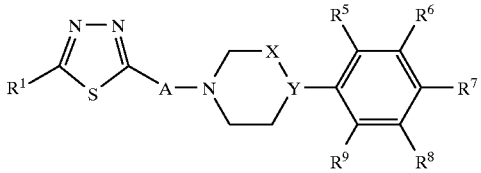

| Ex. No. | R1 | R5 | R6 | R7 | R8 | R9 | X—Y | A |
|---|---|---|---|---|---|---|---|---|
| 59 | $NH_2$ | H | tBut | H | Me | H | $CH_2$—N | S—$(CH_2)_3$— |
| 60 | $NH_2$ | H | tBut | H | Ph | H | $CH_2$—N | S—$(CH_2)_3$— |
| 61 | $NH_2$ | H | tBut | H | 1-Pyrrolyl | H | $CH_2$—N | NH—$(CH_2)_3$— |
| 62 | $NH_2$ | H | iProp | H | 2-Napht | H | CH=C | —$CH_2$—$(CH_2)_3$— |
| 63 | $NH_2$ | H | Et | H | tBut | H | $CH_2$—N | S—$(CH_2)_3$— |
| 64 | $NH_2$ | OMe | tBut | H | H | H | CH=C | —$CH_2$—$(CH_2)_3$— |
| 65 | $NH_2$ | OMe | $CF_3$ | H | H | H | CH=C | S—$(CH_2)_3$— |
| 66 | $NH_2$ | H | $CF_3$ | H | tBut | H | $CH_2$—N | NH—$(CH_2)_3$— |
| 67 | $NH_2$ | OiProp | iProp | H | H | H | $CH_2$—N | S—$(CH_2)_3$— |
| 68 | $NH_2$ | H | H | CN | tBut | H | $CH_2$—N | O—$(CH_2)_3$— |
| 69 | $NH_2$ | H | H | F | tBut | H | CH=C | S—$(CH_2)_3$— |
| 70 | $NH_2$ | H | H | Cl | iProp | H | $CH_2$—N | —$CH_2$—$(CH_2)_3$— |
| 71 | $NH_2$ | H | tBut | H | H | OMe | $CH_2$—N | S—$(CH_2)_3$— |
| 72 | $NH_2$ | OMe | tBut | H | tBut | H | $CH_2$—N | S—$(CH_2)_3$— |
| 73 | $NH_2$ | OMe | tBut | H | $CF_3$ | H | $CH_2$—N | S—$(CH_2)_3$— |
| 74 | $NH_2$ | OMe | $CF_3$ | H | tBut | H | $CH_2$—N | NH—$(CH_2)_3$— |
| 75 | $NH_2$ | H | nProp | CN | tBut | H | CH=C | —$CH_2$—$(CH_2)_3$— |
| 76 | $NH_2$ | H | $CF_3$ | CN | iProp | H | $CH_2$—N | S—$(CH_2)_3$— |
| 77 | $NH_2$ | H | Ph | C=CH | tBut | H | CH=C | —$CH_2$—$(CH_2)_3$— |
| 78 | $NH_2$ | OMe | tBut | CN | H | H | CH=C | S—$(CH_2)_3$— |
| 79 | $NH_2$ | H | tBut | CN | $CF_3$ | OMe | $CH_2$—N | NH—$(CH_2)_3$— |
| 80 | $NH_2$ | OMe | nProp | F | tBut | H | $CH_2$—N | S—$(CH_2)_3$— |
| 81 | $NH_2$ | H | Ph | CN | tBut | Me | $CH_2$—N | O—$(CH_2)_3$— |
| 82 | $NH_2$ | OMe | tBut | F | H | H | CH=C | S—$(CH_2)_3$— |
| 83 | $NH_2$ | H | iProp | H | H | OMe | $CH_2$—N | S—$(CH_2)_3$— |
| 84 | $NH_2$ | H | tBut | H | Me | H | $CH_2$—N | S—$(CH_2)_3$— |
| 85 | $NH_2$ | H | tBut | H | Ph | H | $CH_2$—N | NH—$(CH_2)_4$— |
| 86 | $NH_2$ | H | tBut | H | 1-Pyrrolyl | H | $CH_2$—N | S—$(CH_2)_4$— |
| 87 | $NH_2$ | H | iProp | H | 2-Napht | H | $CH_2$—N | —$CH_2$—$(CH_2)_3$— |
| 88 | $NH_2$ | H | Et | H | tBut | H | $CH_2$—N | S—$(CH_2)_5$— |
| 89 | $NH_2$ | OMe | tBut | H | H | H | $CH_2$—N | O—$(CH_2)_5$— |
| 90 | $NH_2$ | OMe | $CF_3$ | H | H | H | CH=C | NH—$(CH_2)_4$— |
| 91 | $NH_2$ | H | $CF_3$ | H | tBut | H | $CH_2$—N | —$CH_2$—$(CH_2)_4$— |
| 92 | $NH_2$ | OiProp | iProp | H | H | H | CH=C | S—$(CH_2)_3$— |
| 93 | $NH_2$ | H | H | CN | tBut | H | $CH_2$—N | NH—$(CH_2)_3$— |
| 94 | $NH_2$ | H | H | F | tBut | H | $CH_2$—N | S—$(CH_2)_3$— |
| 95 | $NH_2$ | H | H | Cl | iProp | H | CH=C | —$CH_2$—$(CH_2)_3$— |
| 96 | $NH_2$ | H | tBut | H | H | OMe | $CH_2$—N | S—$(CH_2)_3$— |
| 97 | $NH_2$ | OMe | tBut | H | tBut | H | $CH_2$—N | S—$(CH_2)_4$— |
| 98 | $NH_2$ | OMe | tBut | H | $CF_3$ | H | $CH_2$—N | S—$(CH_2)_3$— |
| 99 | $NH_2$ | OMe | $CF_3$ | H | tBut | H | $CH_2$—N | NH—$(CH_2)_5$— |
| 100 | $NH_2$ | H | nProp | CN | tBut | H | CH=C | —$CH_2$—$(CH_2)_3$— |
| 101 | $NH_2$ | H | $CF_3$ | CN | iProp | H | $CH_2$—N | S—$(CH_2)_4$— |
| 102 | $NH_2$ | H | Ph | C=CH | tBut | H | CH=C | —$CH_2$—$(CH_2)_3$— |
| 103 | $NH_2$ | OMe | tBut | CN | H | H | CH=C | S—$(CH_2)_6$— |
| 104 | $NH_2$ | H | tBut | CN | $CF_3$ | OMe | $CH_2$—N | NH—$(CH_2)_3$— |
| 105 | $NH_2$ | OMe | nProp | F | tBut | H | $CH_2$—N | S—$(CH_2)_5$— |
| 106 | $NH_2$ | H | Ph | CN | tBut | Me | $CH_2$—N | O—$(CH_2)_3$— |
| 107 | $NH_2$ | OMe | tBut | F | H | H | CH=C | S—$(CH_2)_4$— |
| 108 | $NH_2$ | H | iProp | H | H | OMe | $CH_2$—N | S—$(CH_2)_3$— |
| 109 | NHMe | H | tBut | H | Me | H | $CH_2$—N | S—$CH_2$—CH=CH—$CH_2$— |
| 110 | NHMe | H | tBut | H | Ph | H | $CH_2$—N | —$CH_2$—$CH_2$—CH=CH—$CH_2$— |
| 111 | NHMe | H | tBut | H | 1-Pyrrolyl | H | $CH_2$—N | S—$CH_2$—CH=CH—$CH_2$— |
| 112 | NHMe | H | iProp | H | 2-Napht | H | $CH_2$—N | NH—$CH_2$—C($CH_3$)=CH—$CH_2$— |
| 113 | NHMe | H | Et | H | tBut | H | $CH_2$—N | S—$CH_2$—C($CH_3$)=CH—$CH_2$— |
| 114 | OH | OMe | tBut | H | H | H | $CH_2$—N | —$CH_2$—$CH_2$—C($CH_3$)=CH—$CH_2$— |
| 115 | OH | OMe | $CF_3$ | H | H | H | $CH_3$—N | NH—$CH_2$—C($CH_3$)=CH—$CH_2$— |
| 116 | OH | H | $CF_3$ | H | tBut | H | $CH_2$—N | S—$CH_2$—CH=CH—$CH_2$— |
| 117 | OH | OiProp | iProp | H | H | H | CH=C | —$CH_2$—$CH_2$—CH=CH—$CH_2$— |
| 118 | OMe | H | H | CN | tBut | H | CH=C | —$CH_2$—$CH_2$—CH=CH—$CH_2$— |
| 119 | OMe | H | H | F | tBut | H | CH=C | S—$CH_2$—C($CH_3$)=CH—$CH_2$— |
| 120 | OMe | H | H | Cl | iProp | H | CH=C | O—$CH_2$—C($CH_3$)=CH—$CH_2$— |
| 121 | OMe | H | tBut | H | H | OMe | CH=C | NH—$CH_2$—C($CH_3$)=CH—$CH_2$— |
| 122 | NHMe | OMe | tBut | H | tBut | H | $CH_2$—N | S—$CH_2$—CH=CH—$CH_2$— |
| 123 | NHMe | OMe | tBut | H | $CF_3$ | H | $CH_2$—N | —$CH_2$—$CH_2$—CH=CH—$CH_2$— |
| 124 | NHMe | OMe | $CF_3$ | H | tBut | H | $CH_2$—N | S—$CH_2$—CH=CH—$CH_2$— |
| 125 | NHMe | H | nProp | CN | tBut | H | $CH_2$—N | NH—$CH_2$—C($CH_3$)=CH—$CH_2$— |

TABLE 4-continued

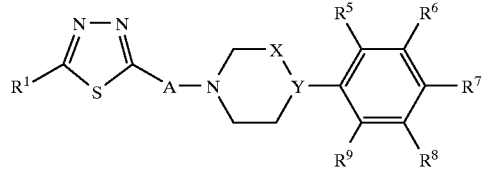

| Ex. No. | R1 | R5 | R6 | R7 | R8 | R9 | X—Y | A |
|---|---|---|---|---|---|---|---|---|
| 126 | NHMe | H | CF$_3$ | CN | iProp | H | CH$_2$—N | S—CH$_2$—C(CH$_3$)=CH—CH$_2$— |
| 127 | OH | H | Ph | C≡CH | tBut | H | CH$_2$—N | —CH$_2$—CH$_2$—C(CH$_3$)=CH—CH$_2$— |
| 128 | OH | OMe | tBut | CN | H | H | CH$_2$—N | NH—CH$_2$—C(CH$_3$)=CH—CH$_2$— |
| 129 | OH | H | tBut | CN | CF$_3$ | OMe | CH$_2$—N | S—CH$_2$—CH=CH—CH$_2$— |
| 130 | OH | OMe | nProp | F | tBut | H | CH=C | —CH$_2$—CH$_2$—CH=CH—CH$_2$— |
| 131 | OMe | H | Ph | CN | tBut | Me | CH=C | —CH$_2$—CH$_2$—CH=CH—CH$_2$— |
| 132 | OMe | OMe | tBut | F | H | H | CH=C | S—CH$_2$—C(CH$_3$)=CH—CH$_2$— |
| 133 | OMe | H | iProp | H | H | OMe | CH=C | S—CH$_2$—C(CH$_3$)=CH—CH$_2$— |

TABLE 5

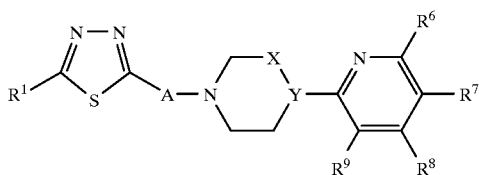

| Ex. No. | R1 | R6 | R7 | R8 | R9 | X—Y | A |
|---|---|---|---|---|---|---|---|
| 134 | NH$_2$ | tBut | H | tBut | H | CH$_2$—N | S—(CH$_2$)$_3$— |
| 135 | OH | tBut | CN | H | H | CH$_2$—N | S—(CH$_2$)$_3$— |
| 136 | NHMe | tBut | H | H | OMe | CH$_2$—N | NH—CH$_2$—CH=CH—CH$_2$— |
| 137 | NH$_2$ | H | CN | tBut | H | CH=C | —CH$_2$—CH$_2$—C(CH$_3$)=CH—CH$_2$— |
| 138 | NHMe | CF$_3$ | H | tBut | H | CH$_2$—N | S—(CH$_2$)$_3$— |
| 139 | NH$_2$ | nProp | H | iProp | H | CH=C | —CH$_2$—(CH$_2$)$_3$— |
| 140 | NHMe | H | H | iProp | OMe | CH=C | S—(CH$_2$)$_3$— |
| 141 | NH$_2$ | tBut | H | tBut | H | CH$_2$—N | NH—CH$_2$—CH=CH—CH$_2$— |
| 142 | NH$_2$ | tBut | CN | H | H | CH$_2$—N | S—(CH$_2$)$_4$— |
| 143 | NHMe | tBut | H | H | OMe | CH$_2$—N | O—(CH$_2$)$_3$— |
| 144 | OH | H | CN | tBut | H | CH=C | S—CH$_2$—C(CH$_3$)=CH—CH$_2$— |
| 145 | NH$_2$ | CF$_3$ | H | tBut | H | CH$_2$—N | —CH$_2$—(CH$_2$)$_3$— |
| 146 | NH$_2$ | nProp | H | iProp | H | CH$_2$—N | S—(CH$_2$)$_3$— |
| 147 | NH$_2$ | nProp | CN | tBut | H | CH$_2$—N | S—(CH$_2$)$_4$— |
| 148 | OH | CF$_3$ | CN | iProp | H | CH$_2$—N | S—(CH$_2$)$_3$— |
| 149 | NHMe | Ph | C≡CH | tBut | H | CH$_2$—N | NH—CH$_2$—CH=CH—CH$_2$— |
| 150 | NH$_2$ | tBut | CN | tBut | H | CH=C | —CH$_2$—CH$_2$—C(CH$_3$)=CH—CH$_2$— |
| 151 | NHMe | tBut | H | nProp | OMe | CH$_2$—N | S—(CH$_2$)$_3$— |
| 152 | NH$_2$ | Ph | H | tBut | OMe | CH=C | —CH$_2$—(CH$_2$)$_5$— |
| 153 | NHMe | CF$_3$ | H | tBut | OMe | CH=C | S—(CH$_2$)$_3$— |
| 154 | NH$_2$ | tBut | F | H | Me | CH$_2$—N | NH—CH$_2$—CH=CH—CH$_2$— |
| 155 | NH$_2$ | nProp | CN | tBut | Me | CH$_2$—N | S—CH$_2$—CH=CH—CH$_2$— |
| 156 | OH | nProp | C≡CH | tBut | OMe | CH=C | —CH$_2$—CH$_2$—C(CH$_3$)=CH—CH$_2$— |
| 157 | NHMe | tBut | CN | H | OMe | CH$_2$—N | S—(CH$_2$)$_4$— |
| 158 | OH | H | H | iProp | OMe | CH$_2$—N | S—(CH$_2$)$_3$— |

TABLE 6

| Ex. No. | R1 | R5 | R7 | R8 | R9 | X—Y | A |
|---|---|---|---|---|---|---|---|
| 159 | NH$_2$ | OMe | H | tBut | H | CH$_2$—N | S—(CH$_2$)$_3$— |
| 160 | OH | OMe | H | CF$_3$ | H | CH$_2$—N | S—(CH$_2$)$_3$— |
| 161 | NHMe | OMe | H | tBut | H | CH$_2$—N | NH—CH$_2$—CH=CH—CH$_2$— |
| 162 | NH$_2$ | H | CN | tBut | H | CH=C | —CH$_2$—CH$_2$—C(CH$_3$)=CH—CH$_2$— |
| 163 | NHMe | H | F | tBut | H | CH$_2$—N | S—(CH$_2$)$_3$— |
| 164 | NH$_2$ | Me | Cl | iProp | H | CH=C | —CH$_2$—(CH$_2$)$_3$— |
| 165 | NHMe | H | H | iProp | OMe | CH=C | S—(CH$_2$)$_3$— |
| 166 | NH$_2$ | H | H | tBut | OMe | CH$_2$—N | NH—CH$_2$—CH=CH—CH$_2$— |
| 167 | NH$_2$ | CN | H | CF$_3$ | H | CH$_2$—N | S—(CH$_2$)$_4$— |
| 168 | NHMe | H | CN | H | OMe | CH$_2$—N | O—(CH$_2$)$_3$— |
| 169 | OH | H | H | tBut | OEt | CH=C | S—CH$_2$—C(CH$_3$)=CH—CH$_2$— |
| 170 | NH$_2$ | H | CN | tBut | H | CH$_2$—N | —CH$_2$—(CH$_2$)$_3$— |
| 171 | NH$_2$ | Me | H | iProp | H | CH$_2$—N | S—(CH$_2$)$_3$— |
| 172 | NH$_2$ | OMe | CN | tBut | H | CH$_2$—N | S—(CH$_2$)$_4$— |
| 173 | NH$_2$ | OMe | Me | tBut | H | CH$_2$—N | S—(CH$_2$)$_3$— |
| 174 | NHMe | H | CN | tBut | OMe | CH$_2$—N | NH—CH$_2$—CH=CH—CH$_2$— |
| 175 | NH$_2$ | Me | H | tBut | OMe | CH=C | —CH$_2$—CH$_2$—C(CH$_3$)=CH—CH$_2$— |
| 176 | NH$_2$ | H | Cl | CF$_3$ | Me | CH$_2$—N | S—(CH$_2$)$_5$— |
| 177 | NHMe | OMe | CN | tBut | Me | CH=C | —CH$_2$—(CH$_2$)$_3$— |
| 178 | OH | Me | Me | iProp | Me | CH=C | S—(CH$_2$)$_4$— |
| 179 | OH | OMe | H | iProp | H | CH$_2$—N | S—(CH$_2$)$_3$— |

TABLE 7

| Ex. No. | R1 | R5 | R6 | R8 | R9 | X—Y | A |
|---|---|---|---|---|---|---|---|
| 180 | NH$_2$ | H | tBut | tBut | H | CH$_2$—N | S—(CH$_2$)$_3$— |
| 181 | OH | H | tBut | Ph | H | CH$_2$—N | S—(CH$_2$)$_3$— |
| 182 | NHMe | H | tBut | 1-Pyrrolyl | H | CH$_2$—N | NH—CH$_2$—CH=CH—CH$_2$— |
| 183 | NH$_2$ | H | nPropyl | tBut | H | CH=C | —CH$_2$—CH$_2$—C(CH$_3$)=CH—CH$_2$— |
| 184 | NHMe | H | CF$_3$ | tBut | H | CH$_2$—N | S—(CH$_2$)$_3$— |
| 185 | NH$_2$ | H | 2-Napht | tBut | H | CH=C | —CH$_2$—(CH$_2$)$_3$— |
| 186 | NHMe | OMe | tBut | H | H | CH=C | S—(CH$_2$)$_3$— |
| 187 | NH$_2$ | OMe | iProp | H | H | CH$_2$—N | NH—CH$_2$—CH=CH—CH$_2$— |
| 188 | NH$_2$ | OMe | H | CF$_3$ | H | CH$_2$—N | S—(CH$_2$)$_4$— |
| 189 | NHMe | H | tBut | H | OMe | CH$_2$—N | O—(CH$_2$)$_3$— |
| 190 | OH | H | iProp | H | Me | CH=C | S—CH$_2$—C(CH$_3$)=CH—CH$_2$— |
| 191 | NH$_2$ | CN | tBut | H | H | CH$_2$—N | —CH$_2$—(CH$_2$)$_3$— |
| 192 | NH$_2$ | H | H | CF$_3$ | Me | CH$_2$—N | S—(CH$_2$)$_3$— |
| 193 | NHMe | OMe | tBut | iProp | H | CH$_2$—N | S—(CH$_2$)$_4$— |
| 194 | OH | OMe | CF$_3$ | tBut | H | CH$_2$—N | NH—CH$_2$—CH=CH—CH$_2$— |
| 195 | NH$_2$ | Me | tBut | nProp | H | CH=C | —CH$_2$—CH$_2$—C(CH$_3$)=CH—CH$_2$— |
| 196 | NH$_2$ | Me | tBut | H | OMe | CH$_2$—N | S—(CH$_2$)$_5$— |
| 197 | NH$_2$ | OMe | tBut | tBut | OMe | CH=C | —CH$_2$—(CH$_2$)$_3$— |
| 198 | NH$_2$ | Me | CF$_3$ | tBut | OMe | CH=C | S—(CH$_2$)$_4$— |
| 199 | OH | H | nProp | tBut | H | CH$_2$—N | S—(CH$_2$)$_3$— |

TABLE 8

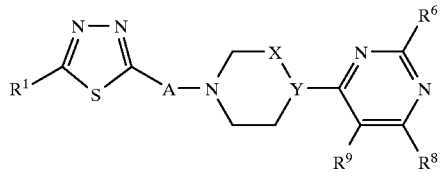

| Ex. No. | R1 | R6 | R8 | R9 | X—Y | A |
|---|---|---|---|---|---|---|
| 200 | NH₂ | tBut | Ph | H | CH₂—N | —CH₂—(CH₂)₃— |
| 201 | NH₂ | tBut | 2-Napht | H | CH₂—N | S—CH₂—C(CH₃)═CH—CH₂— |
| 202 | NH₂ | tBut | 1-Pyrrolyl | H | CH₂—N | S—(CH₂)₃— |
| 203 | NHMe | tBut | cHex | H | CH═C | —CH₂—(CH₂)₃— |
| 204 | NH₂ | tBut | nHex | H | CH₂—N | S—(CH₂)₅— |
| 205 | NH₂ | tBut | H | OMe | CH₂—N | —CH₂—(CH₂)₃— |
| 206 | NHMe | iProp | H | OMe | CH₂—N | S—CH₂—C(CH₃)═CH—CH₂— |
| 207 | NH₂ | H | CH₃ | OMe | CH═C | NH—(CH₂)₃— |
| 208 | NH₂ | H | iProp | OMe | CH₂—N | O—CH₂—CH═CH—CH₂— |
| 209 | NH₂ | tBut | tBut | OMe | CH₂—N | —CH₂—(CH₂)₃— |
| 210 | NHMe | tBut | iProp | OMe | CH₂—N | S—CH₂—C(CH₃)═CH—CH₂— |
| 211 | NH₂ | tBut | Ph | Cl | CH₂—N | S—(CH₂)₄— |
| 212 | NH₂ | 2-Napht | tBut | Me | CH═C | —CH₂—(CH₂)₃— |
| 213 | NH₂ | tBut | CF₃ | OMe | CH₂—N | S—(CH₂)₃— |
| 214 | NH₂ | tBut | H | CH₃ | CH₂—N | S—(CH₂)₃— |
| 215 | NH₂ | tBut | Ph | H | CH₂—N | S—(CH₂)₃— |
| 216 | NH₂ | tBut | 2-Napht | H | CH═C | NH—(CH₂)₃— |
| 217 | NH₂ | tBut | 1-Pyrrolyl | H | CH₂—N | O—CH₂—C(CH₃)═CH—CH₂— |
| 218 | NH₂ | tBut | cHex | H | CH₂—N | —CH₂—(CH₂)₃— |
| 219 | OH | tBut | nHex | H | CH₂—N | S—(CH₂)₄— |
| 220 | OH | tBut | H | OMe | CH═C | S—(CH₂)₄— |
| 221 | OMe | iProp | H | OMe | CH₂—N | —CH₂—CH₂—CH═CH—CH₂— |
| 222 | OMe | H | CH₃ | OMe | CH₂—N | —CH₂—(CH₂)₃— |
| 223 | NCH₂Ph | H | iProp | OMe | CH₂—N | S—CH₂—C(CH₃)═CH—CH₂— |
| 224 | OH | tBut | tBut | OMe | CH₂—N | —CH₂—(CH₂)₄— |
| 225 | OH | tBut | iProp | OMe | CH₂—N | S—CH₂—CH═CH—CH₂— |
| 226 | OMe | Ph | tBut | Cl | CH₂—N | S—(CH₂)₅— |
| 227 | OMe | 2-Napht | tBut | Me | CH═C | —CH₂—(CH₂)₃— |
| 228 | NCH₂Ph | tBut | CF₃ | OMe | CH₂—N | S—(CH₂)₄— |
| 229 | NHMe | tBut | H | CH₃ | CH═C | S—(CH₂)₃— |

Examples of Pharmaceutical forms:

A) Tablets

Tablets of the following composition were compressed in a tabletting machine in a conventional manner 40 mg of substance of Example 1

120 mg of corn starch 13.5 mg of gelatin 45 mg of lactose 2.25 mg of Aerosil® (chemically pure silica in submicroscopically fine dispersion)

6.75 mg of potato starch (as 6% strength paste)

B) Sugar-coated tablets 20 mg of substance of Example 4

60 mg of core composition 70 mg of sugar-coating composition

The core composition comprises 9 parts of corn starch, 3 parts of lactose and 1 part of vinylpyrrolidone/vinyl acetate 60:40 copolymer. The sugar-coating composition comprises 5 parts of sucrose, [lacuna] parts of corn starch, 2 parts of calcium carbonate and 1 part of talc. The sugar-coated tablets produced in this way are subsequently provided with an enteric coating.

Biological investigations - receptor-binding studies

1) D₃ binding assay

Cloned human D₃ receptor-expressing CCL 1.3 mouse fibroblasts obtained from Res. Biochemicals Internat. One Strathmore Rd., Natick, Mass. 01760-2418 USA, were used for the binding studies.

Cell preparation

The D₃-expressing cells were grown in RPMI-1640 containing 10% fetal calf serum (GIBCO No. 041-32400 N); 100 U/ml penicillin and 0.2% streptomycin (GIBCO BRL, Gaithersburg, Md., USA). After 48 h, the cells were washed with PBS and incubated with 0.05% trypsin-containing PBS for 5 min. Neutralization with medium was then carried out, and the cells were collected by centrifugation at 300×g. To lyze the cells, the pellet was briefly washed with lysis buffer (5 mM tris-HCl, pH 7.4, with 10% glycerol) and then incubated in a concentration of $10^7$ cells/ml of lysis buffer at 4° C. for 30 min. The cells were centrifuged at 200×g for 10 min and the pellet was stored in liquid nitrogen.

Binding assays

For the D₃ receptor-binding assay, the membranes were suspended in incubation buffer (50 mM tris-HCl, pH 7.4, with 120 mM NaCl, 5 mM KCl, 2 mM CaCl₂, 2mM MgCl₂, 10 μM quinolinol, 0.1% ascorbic acid and 0.1% BSA) in a concentration of about $10^6$ cells/250 μl of assay mixture and incubated at 30° C. with 0.1 nM [125]iodosulpiride in the presence and absence of test substance. The non-specific binding was determined using $10^{-6}$ M spiperone.

After 60 min, the free and the bound radioligand was separated by filtration through GF/B glass fiber filters (Whatman, England) on a Skatron cell collector (Skatron, Lier, Norway), and the filters were washed with ice-cold tris-HCl buffer, pH 7.4. The radioactivity collected on the filters was quantified using a Packard 2200 CA liquid scintillation counter.

The $K_i$ values were determined by non-linear regression analysis using the LIGAND program.

2) $D_2$ binding assay

Membrane preparation a) Nucleus caudatus (bovine)

Nucleus caudatus was removed from bovine brain and washed with ice-cold 0.32 M sucrose solution. After determination of the weight, the material was comminuted and homogenized in 5–10 volumes of sucrose solution using a Potter-Evehjem [sic] homogenizer (500 rpm). The homogenate was centrifuged at 3,000×g for 15 minutes (4° C.), and the resulting supernatant was subjected to another 15-minute centrifugation at 40,000×g. The residue was then washed twice, by resuspension and centrifugation, with 50 mM tris-HCl, pH 7.4. The membranes were stored in liquid nitrogen until used.

b) Striatum (rat)

Striati from Sprague-Dawley rats were washed in ice-cold 0.32 M sucrose solution. After determination of the weight, the parts of the brain were homogenized in 5–10 volumes of sucrose solution using a Potter-Elvehjem homogenizer (500 rpm). The homogenate was centrifuged at 40,000×g for 10 minutes (4° C.), and then the residue was washed several times, by resuspension and centrifugation, with 50 mM tris-HCl, 0.1 mM EDTA and 0.01% ascorbic acid (pH 7.4). The washed residue was resuspended in the abovementioned buffer and incubated at 37° C. for 20 minutes (to break down the endogenous dopamine). The membranes were then washed twice with buffer and portions were frozen in liquid nitrogen. The membrane preparation was stable for a maximum of one week.

Binding assay a) $^3$H-Spiperone ($D_{2low}$)

Nucleus caudatus membranes were taken up in incubation buffer (mM: tris-HCl 50, NaCl 120, KCl 5, $MgCl_2$ 1, $CaCl_2$ 2, pH 7.4). Various mixtures, each of 1 ml, were prepared:

Total binding: 400 μg of membranes+0.2 nmol/l $^3$H-spiperone (Du Pont de Nemours, NET-565).

Non-specific binding: as mixtures for total binding+10 μM (+)-butaclamol.

Test substance: as mixtures for total binding+increasing concentrations of test substance.

After incubation at 25° C. for 60 minutes, the mixtures were filtered through GF/B glass fibre filters (Whatman, England) on a Skatron cell collector (from Zinsser, Frankfurt), and the filters were washed with ice-cold 50 mM tris-HCl buffer, pH 7.4. The radioactivity collected on the filters was quantified using a Packard 2200 CA liquid scintillation counter.

The $K_i$ values were determined by non-linear regression analysis using the LIGAND program or by conversion of the $IC_{50}$ values using the formula of Cheng and Prusoff.

b) $^3$H-ADTN ($D_{2high}$)

Striatum membranes were taken up in incubation buffer (50 mM tris-HCl, pH 7.4, 1 mM $MnCl_2$ and 0.1% ascorbic acid).

Various mixtures, each of 1 ml, were prepared.

Total binding: 300 μg wet weight+1 nM $^3$H-ADTN (Du Pont de Nemours, customer synthesis)+100 nM SCH 23390 (occupation of $D_1$ receptors).

Non-specific bindings: as mixtures for total binding+50 nM spiperone.

Test substance: as mixtures for total binding+increasing concentrations of test substance.

After incubation at 25° C. for 60 minutes, the mixtures were filtered through GF/B glass fibre filters (Whatman, England) on a Skatron cell collector (from Zinsser, Frankfurt), and the filters were washed with ice-cold 50 mM tris-HCl buffer, pH 7.4.

The radioactivity collected on the filters was quantified using a Packard 2200 CA liquid scintillation counter.

The evaluation took place as under a).

In these assays, the compounds according to the invention show very good affinities and high selectivities for the $D_3$ receptor. The results obtained for representative compounds are compiled in the following Table 9.

TABLE 9

| | Receptor binding | | |
|---|---|---|---|
| Example No. | $D_3$ $^{125}$I-sulpiride $K_i$ [nM] | $D_2$ $^3$H-spiperone $K_i$ [mM] | Selectivity $K_iD_2/K_iD_3$ |
| 2 | 1.4 | 65 | 46 |
| 13 | 0.6 | 25 | 41 |
| 16 | 10.9 | 402 | 36 |
| 23 | 6.3 | 200 | 31 |
| 49 | 6.5 | 560 | 86 |
| 51 | 8.3 | 500 | 62 |
| 53 | 2.95 | 145 | 50 |
| 56 | 27.0 | 3,500 | 70 |
| 58 | 1.7 | 225 | 132 |

We claim:

1. A method for treating disorders which respond to dopamine $D_3$ receptor antagonists or agonists which comprises administering to a person requiring such treatment an effective amount of a member selected from the group consisting of thiazole and thiadiazole compounds of the formula I:

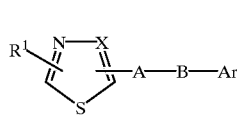

where

A is a straight-chain or branched $C_3$–$C_{14}$-alkylene group which comprises at least one group selected from O, S, and NR, B is a radical of the formula:

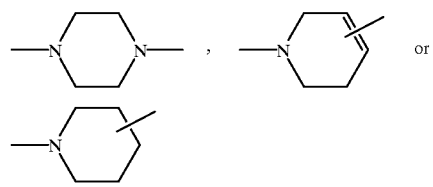

$R^1$ is H, $NR^2R^3$, or $C_1$–$C_8$-alkyl;

$R^2$ is H or $C_1$–$C_8$-alkyl, which is unsubstituted or substituted by OH;

$R^3$ has the meanings indicated for $R^2$;

X is N;

Ar is phenyl, pyridyl or pyrimidyl where Ar may have one or two substituents which are selected, independently of one another, from $OR^3$, $C_1$–$C_8$-alkyl, halogen, CN, $NO_2$, $CF_3$, $CHF_2$, phenyl, and a 5-membered heterocyclic aromatic ring having 1 or 2 hetero atoms selected from O, S and N, and the salts thereof with physiologically tolerated acids.

2. A method as claimed in claim 1 which comprises administering a member selected from the group consisting of compounds of the formula I where $R^1$ is H, or $NR^2R^3$, where $R^2$ and $R^3$ are, independently of one another, H or $C_1$–$C_8$-alkyl; and A is $C_3$–$C_{12}$-alkylene which comprises at least one group selected from O, S, and $NR^3$.

3. A method as claimed in claim 1 of compounds of the formula I where
B is

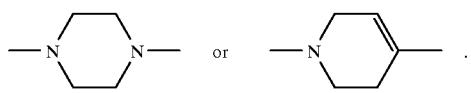

4. A method as claimed in claim 1 of compound of the formula I where
Ar is phenyl which has one or two substituents which are selected, independently of one another, from H, $C_1$–$C_8$-alkyl, phenyl, pyrrolyl, $CHF_2$, $CF_3$, halogen, $NO_2$, CN, OH, $OC_1$–$C_8$-alkyl.

5. A method as claimed in claim 4, where Ar has one or two substituents which are in position 3 or position 3,5.

6. A method as claimed in any of claims 1 to 5 of compounds of the formula I where Ar is pyrimidinyl which has one or two substituents which are selected, independently of one another, from H, $C_1$–$C_8$-alkyl, phenyl, pyrrolyl, OH, $OC_1$–$C_8$-alkyl, $CHF_2$, $CF_3$ and halogen.

7. A method as claimed in claim 1 of compounds of the formula I where Ar is pyridinyl which has one or two substituents which are selected, independently of one another, from H, $C_1$–$C_1$-alkyl, phenyl, pyrrolyl, OH, $OC_1$–$C_8$-alkyl, $CHF_2$, $CF_3$, CN and halogen.

8. A compound of the formula I:

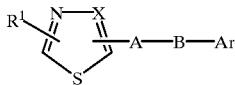

(I)

where A is a straight-chain or branched $C_7$–$C_{14}$-alkylene group which comprises a group which is selected from O, S, and $NR^3$ and, $R^1$, $R^2$, $R^3$, B and Ar have the meanings stated in claim 1.

9. A process for preparing compounds as claimed in claim 8, which comprises i) reacting a compound of the general formula II:

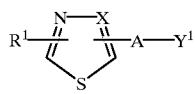

where $Y^1$ is a conventional leaving group, with a compound of the general formula III:

ii) to prepare a compound of the formula I where A comprises an oxygen or sulfur atom or $NR^3$,
a) reacting a compound of the general formula IV:

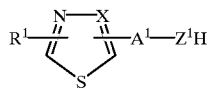

where $Z^1$ is O, S or $NR^3$, and $A^1$ is $C_0$–$C_{18}$-alkylene, with a compound of the general formula VI

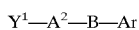

where $Y^1$ has the abovementioned meanings, and $A^2$ is $C_1$–$C_{14}$-alkylene, where $A^1$ and $A^2$ together have 7 to 14 carbon atoms;
and all the other substituents have the same meaning as defined in claim 1.

10. A pharmaceutical composition containing at least one compound of the formula I as claimed in claim 8 with or without physiologically acceptable salts.

11. A process for preparing compounds as claimed in claim 8, which comprises i) reacting a compound of the general formula II:

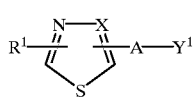

where $Y^1$ is a conventional leaving group, with a compound of the general formula III:

* * * * *

UNITED STATES PATENT AND TRADEMARK OFFICE
CERTIFICATE OF CORRECTION

PATENT NO. : 5,958,923

DATED : September 28, 1999

INVENTOR(S) : HELLENDAHL et al.

It is certified that error appears in the above-identified patent and that said Letters Patent is hereby corrected as shown below:

Col. 29,. claim 6, line 28, delete "any of claims 1 to 5" and substitute --claim 1--.

Col. 30, line 8, "where Y' " should be --where $Y^1$--.

Signed and Sealed this

First Day of February, 2000

Q. TODD DICKINSON

*Attest:*

*Attesting Officer*   *Acting Commissioner of Patents and Trademarks*